Figure 1:
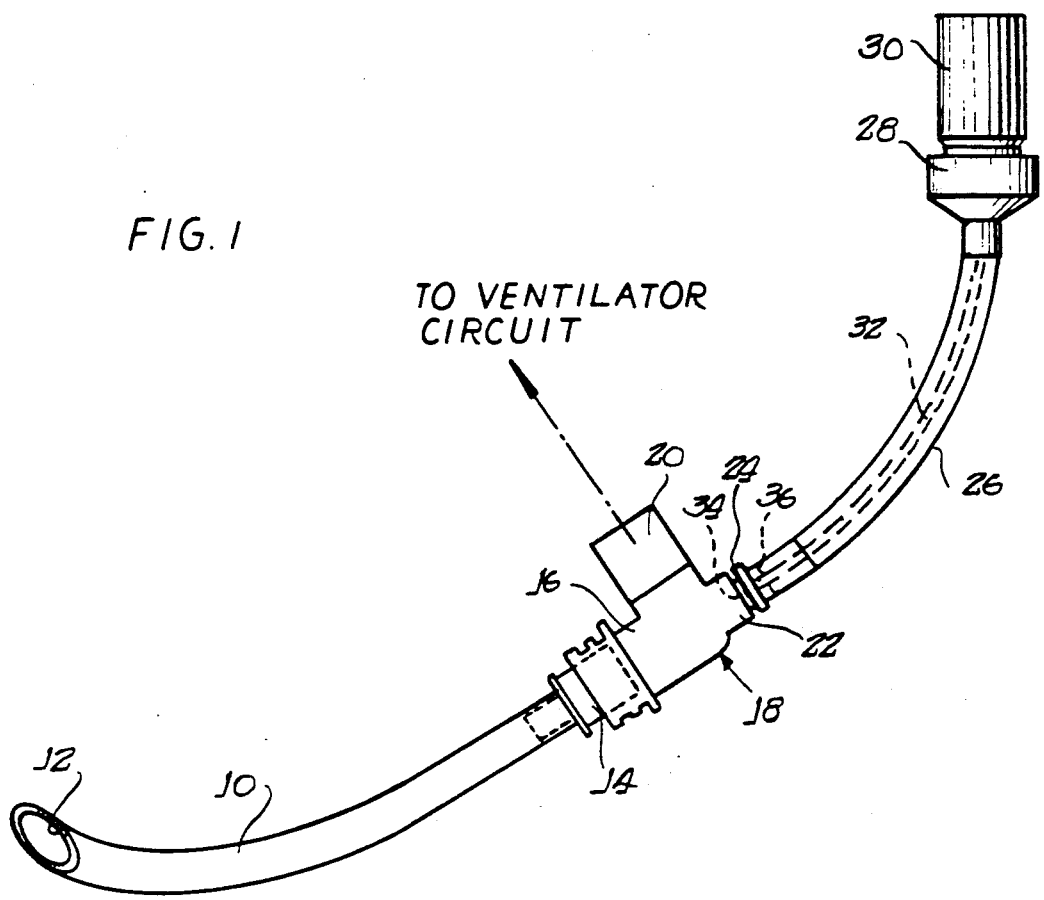

United States Patent [19]

Foley

[11] Patent Number: 5,078,131
[45] Date of Patent: Jan. 7, 1992

[54] INTRODUCTION OF MEDICATION IN VENTILATOR CIRCUIT

[75] Inventor: Martin P. Foley, London, Canada
[73] Assignee: Trudell Medical, London, Canada
[21] Appl. No.: 526,234
[22] Filed: May 21, 1990
[51] Int. Cl.$^5$ ............................................. A61M 16/04
[52] U.S. Cl. ........................... 128/203.15; 128/207.14; 128/200.14; 604/163
[58] Field of Search .............. 128/207.14, 207.15, 128/203.12, 203.15, 912, 200.23, 200.14, 204.18, 911, DIG. 26; 604/163

[56] References Cited

U.S. PATENT DOCUMENTS

| | | | |
|---|---|---|---|
| 4,510,933 | 4/1985 | Wendt et al. | 128/207.14 |
| 4,669,463 | 6/1987 | McConnell | 128/207.14 |
| 4,878,893 | 11/1989 | Chin | 128/4 |

Primary Examiner—David A. Wiecking
Assistant Examiner—Stephen R. Funk
Attorney, Agent, or Firm—Robert M. Wolters

[57] ABSTRACT

Apparatus is provided for injecting medication into a ventilator circuit. An elbow connects an endotracheal tube to the external ventilator circuit. A port in the elbow is connected to a flexible sheath leading to an actuator receiving an MDI canister. A catheter extends from the actuator substantially through the sheath to a position adjacent the elbow. When it is desired to inject medication, the actuator is moved to a position adjacent the elbow, thus projecting the discharge end of the catheter to a position within the endotracheal tube, but short of the open end thereof.

4 Claims, 1 Drawing Sheet

INTRODUCTION OF MEDICATION IN VENTILATOR CIRCUIT

BACKGROUND OF THE INVENTION

A person who is ill may often having trouble breathing by himself. In such a case it is necessary to use a ventilator. This will include mechanical or forced inhalation, and generally also includes an endotracheal tube extending through the patient's mouth and into his tracea. Provision may also be made for either voluntary or mechanical exhalation through the endotracheal tube. Patients under ventilator support or coming out of anesthesia often have bronchospasms and thus need a brochodilator. In past practice, it has often been necessary to open the ventilator circuit in order to introduce a brochodilator. This takes time, and frequently there is a crisis condition where very little time is available for administrating a brochodilator. One effort to solve that problem is exemplified in the copending application of William R. Shene, Ser. No. 07/342,309, filed Apr. 25, 1989 for "Inhalation Chamber in Ventilator Circuit" (allowed Jan. 22, 1990), now U.S. Pat. No. 4,983,210 assigned to the same assignee as the present application, namely Trudell Medical, Partnership having a place of business in London, Ontario, Canada. The Shene apparatus utilizes an accordian pleated cylinder into which medication may be injected, combined with a telescoping connection for incorporating the cylinder in the ventilator circuit, or for excluding it therefrom, without the necessity of opening the ventilator circuit.

OBJECTS AND SUMMARY OF THE PRESENT INVENTION

It is an object of the present invention to provide a ventilator circuit including an endotracheal tube with a catheter or tube retractable from the endotracheal tube, or extendable thereinto for discharge of medication internally of the endotracheal tube, but relatively adjacent the open end thereof.

It is a further object of the present invention to provide a ventilator circuit as in the preceeding object wherein a measured dose inhaler canister cooperates with a catheter or tube, the catheter opening into the ventilator circuit, but normally retracted therefrom, wherein the catheter is insertable into the endotracheal tube without opening of the ventilator circuit.

In carrying out the foregoing and other objects of the present invention I utilize a generally conventional endotracheal tube. The endotracheal tube is connected to the ventilator circuit by an elbow having a port therein aligned with the endotracheal tube. The port has a flexible sheath extending therefrom to an actuator carrying a measured dose inhaler (MDI) canister. A catheter or MDI tube extends from the actuator through the flexible sheath to the vicinity of the elbow. A centering guide is provide at the end of the MDI tube remote from the actuator. The actuator and the canister can be moved toward the elbow, thus projecting the MDI tube through the elbow and through a major portion of the endotrachal tube when it is desired to meter medication to the patient. The catheter at its furthest advanced position is still well short of the opening at the end of the endotracheal tube, whereby it is protected from any outside influence and be reused as needed. The centering device maintains the MDI tube substantially coaxial with the endotracheal tube. The actuator and MDI tube can be readily withdrawn when the patient's need for medication has passed, and the MDI tube is maintained in sterile condition by the surrounding flexible sheath.

THE DRAWINGS

Figure 2:
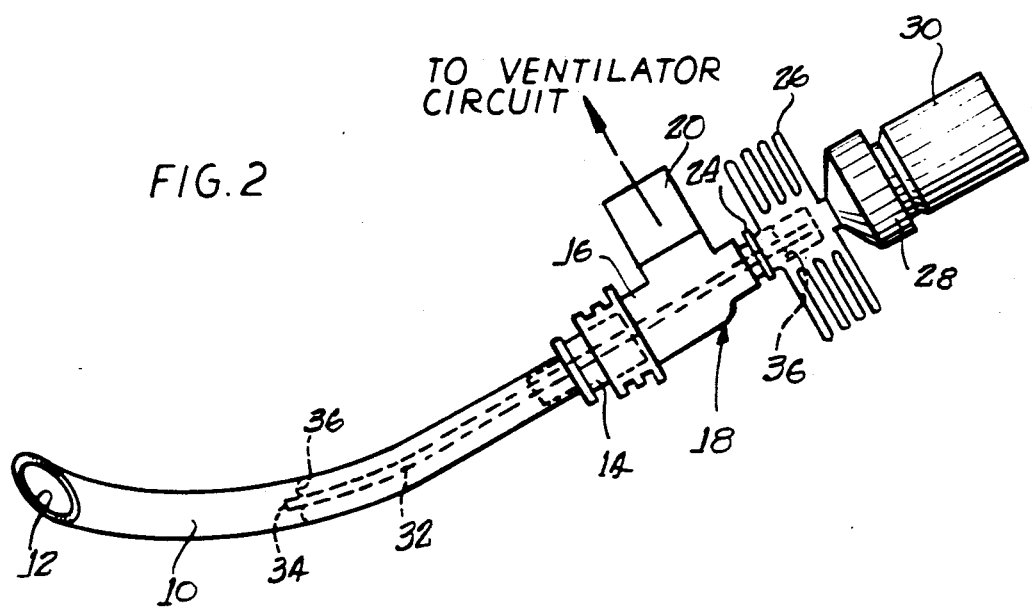

The present invention will best be understood from the following specification when taken in connection with the accompanying drawings wherein:

FIG. 1 is a side view of the present invention with the medication injecting structure in withdrawn or standby condition; and FIG. 2 is a view similar to FIG. 1 but showing the medication injecting structure moved into medication injecting position.

DETAILED DISCLOSURE OF THE ILLUSTRATED EMBODIMENT

Turning now in greater particularity to the drawings, and first to FIG. 1, there will be seen a generally conventional endotracheal tube 10 having an opening 12 at the end thereof. The opposite end of the endotracheal tube is connected by a fitting 14 to the lateral arm 16 of an elbow 18. The vertical stem 20 of the elbow is connected to a conventional ventilator circuit as indicated.

The elbow 18 is provided with a port 22 opposite to and in alignment with the arm 16. A fitting 24 connects a flexible sheath 26 to the port 22 of the elbow 16, the opposite end of the sheath being connected to an actuator 28 in which is received an metered dose inhaler (MDI) canister 30 of suitable medication for bronchial dilation, generically a beta-agonist, epinepherine being a typical example. A catheter or MDI tube 32 extends from the actuator 28 through the flexible sheath 26 substantially to the elbow 18, the end 34 thereof being just short of the elbow and having a centering device 36 of flexible nature such as plastic resin lightly gripping the catheter and slidable within the fitting 24, and subsequently within the endotracheal tube 10. With the position of parts as shown in FIG. 1, the endotracheal tube can be inserted in a patient's trachea, and normal ventilation can be conducted through the elbow and the endotracheal tube.

In the event that it should become necessary or desirable to provide the patient with a medication for bronchial dilation, all that is necessary is to move the parts from the position shown in FIG. 1 to the position shown in FIG. 2. The catheter or MDI tube 32 is projected into the endotracheal tube, somewhat more than one-half the length of the endotracheal tube, but with the end 34 of the cateter 32 still well short of the open end 12 of the endotracheal tube. The MDI canister is then depressed into the actuator to release a metered or measured dose of medication. This medication will pass through the catheter or MDI tube 32, and be released into the endotracheal tube relatively adjacent the open end 12 thereof, whereby it will be inhaled along with the air/oxygen mixure entering the patient's lungs from the ventilator circuit.

When the need for bronchial dilator medication has passed, the parts may be withdrawn from the position of FIG. 2 to the original position of FIG. 1. The sheath 26 protects the catheter from outside air, and retains it in sterile condition. It therefore can be again moved from the position of FIG. 1 to that of FIG. 2 for further administration of bronchial dilator medication. The flexible tube 26 is shown in FIG. 2 in an accordian pleated shape, and it may be preshaped to some extent to effect such pleating, or it may fall into a rather rough pleated configuration. The important thing is that it is capable of being materially shortened so that the catheter may extend more than half way through the endotracheal tube. It will be noted that the end of the actuator 28 engages the fitting 24 to limit the extent of movement of the catheter 32 through the endotraheal tube.

The present invention overcomes the problem of prior art of assured delivery of medication to the tracheal/bronchi respiratory system of mechanically ventilated patients. The apparatus among other things reduces trauma and risks, due to disconnection of the ventilator circuit in the prior art. The present invention further prevents interruption of positive ventilatin pressure by the existence of manipulation of the tube or catheter. It comprises relatively inexpensive, facile and reliable componets. Sterility of the tube or catheter is preserved, and the structure is readily assembled and disassembled. The central guide of the tube within the endotracheal tube provides for centering of the catheter. Termination of the catheter short of the opening of the endotracheal tube insures that larger particles over 5 microns, which are not beneficial to the patient, will be eliminated. The large drug and surfactant particles adhere to the inner surface of the endotracheal tube.

A universal site is provided in a form of the actuator which accepts all meter dose inhalers. The present invention is greatly simplified relative to prior art devices, it is highly reliable, it is easy to use, and it is cost effective, contamination free, and preserves the sterility, while being safe and effective in use.

The present invention is equally adatable for use with pediatric ventilation apparatus in which a 3 to 6 mm endotracheal tube is used, and with adult ventilators in which endotracheal tubes of 6 to 9 mm are used.

The specific example of the invention as herein shown and described is for illustrative purposes. It will apparent that medications other than bronchial dilators could be injected, if required. Various changes in structure will no doubt occur to those skilled in the art, and will be understood as forming a part of the present invention insofar as they fall within the spirit and scope of the appended claims.

The invention is claimed as follows:

1. Apparatus for injecting medication into a ventilator circuit comprising a connector adapted for connection to a ventilator circuit, an endotracheal tube having an open end and having a second end connected to said connector for connection with said ventilator circuit, said connector having a port substantially aligned with said endotracheal tube, a flexible sheath having two open ends and connected at one end to said connector adjacent said port, an actuator connected to the other end of said sheath and adapted for receipt of a metered dose medication canister, a catheter disposed within said sheath and having a first end connected to said actuator for receipt of medication from the metered dose medication canister and having a second end adjacent said connector, said catheter being movable into said endotracheal tube for discharge of medication into said endotracheal tube for inhalation of medication from said endotracheal tube, first stop means fixed adjacent said connector and second stop means adjacent said actuator, there being a first predetermined length from said first stop means to said open of said endotracheal tube and there being a second predetermined length from said second stop means to said second end of said catheter, said second predetermined length being substantially less than said first predetermined length, whereby said second stop means engages said first stop means upon movement of said catheter into said endotracheal tube to limit disposition of said catheter within said endotracheal tube with said catheter second end adjacent a mid portion of said endotracheal tube and substantially short of the open end of said endotracheal tube, and a guide acting between said catheter adjacent said second end of said catheter and said endotracheal tube for substantially centering said catheter second end within said endotracheal tube.

2. Apparatus as set forth in claim 1 wherein the first stop means comprises an end surface on said connector.

3. Apparatus as set forth in claim 1 wherein said second stop means comprises an end surface on said actuator.

4. Apparatus as set forth in claim 1 wherein at least a part of said sheath folds into an accordian pleated shape upon movement of said catheter into said endotracheal tube.

* * * * *